(12) United States Patent
Bentz

(10) Patent No.: US 11,896,598 B2
(45) Date of Patent: *Feb. 13, 2024

(54) APPETITE SUPPRESSANT COMPOSITIONS AND METHODS THEREOF

(71) Applicant: Red Mountain Med Spa, LLC, Scottsdale, AZ (US)

(72) Inventor: Suzanne Bentz, Scottsdale, AZ (US)

(73) Assignee: RED MOUNTAIN MED SPA, LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/733,690

(22) Filed: Apr. 29, 2022

(65) Prior Publication Data

US 2022/0249505 A1    Aug. 11, 2022

Related U.S. Application Data

(63) Continuation of application No. 16/808,084, filed on Mar. 3, 2020, now Pat. No. 11,344,556.

(51) Int. Cl.
| | | |
|---|---|---|
| *A61K 31/5377* | (2006.01) | |
| *A61K 31/135* | (2006.01) | |
| *A61K 9/48* | (2006.01) | |
| *A61K 47/38* | (2006.01) | |
| *A61K 9/00* | (2006.01) | |
| *A61K 47/42* | (2017.01) | |
| *A61P 43/00* | (2006.01) | |

(52) U.S. Cl.
CPC ........ *A61K 31/5377* (2013.01); *A61K 9/0053* (2013.01); *A61K 9/4808* (2013.01); *A61K 31/135* (2013.01); *A61K 47/38* (2013.01); *A61K 47/42* (2013.01); *A61P 43/00* (2018.01)

(58) Field of Classification Search
CPC .............. A61K 31/135; A61K 31/5377; A61K 47/38; A61K 47/42; A61K 9/0053; A61K 9/4808; A61K 9/4866; A61P 43/00
See application file for complete search history.

(56) References Cited

U.S. PATENT DOCUMENTS

| | | | | |
|---|---|---|---|---|
| 5,019,594 A | * | 5/1991 | Wurtman | A61K 31/195 514/561 |
| 5,534,272 A | * | 7/1996 | Bernstein | A23G 4/064 426/3 |
| 5,543,405 A | | 8/1996 | Keown | |
| 2004/0204472 A1 | | 10/2004 | Briggs | |
| 2012/0310211 A1 | | 12/2012 | Du Toit et al. | |
| 2021/0275536 A1 | | 9/2021 | Bentz | |
| 2022/0000763 A1 | | 1/2022 | Dely | |

FOREIGN PATENT DOCUMENTS

| | | | |
|---|---|---|---|
| CA | 2174422 | | 4/1995 |
| CN | 101283804 | * | 10/2008 |
| CN | 104736147 | * | 6/2015 |
| WO | WO 0025806 | * | 5/2000 |

OTHER PUBLICATIONS

Wolff, Burger's Medicinal Chemistry and Drug Discovery, 5th Edition, vol. I Principles and Practice, pp. 975-977, 1995 (Year: 1995).*
Banker et al., Prodrugs, Modern Pharmaceutics, Third Edition and Expanded, pp. 451 and 596 (1996) (Year: 1996).*
CN 104736147—English translation document, 2015 (Year: 2015).*
CIPO; Examination Report dated Jul. 12, 2021 in CA Application No. 3074541.
CIPO; Examination Report dated Dec. 13, 2021 in CA Application No. 3074541.
Gavilanes, G., "Can You Use Collagen For Weight Loss?", https://www.vitalproteins.com/blogs/stay-vital/collagen-for-weight-loss Jan. 21, 2019 (Jan. 21, 2019).
Lynn, L., "Does Taking A Collagen Supplement Hurt Your Weight Loss?", https://lynfit.com/blogs/news/does-taking-a-collagen-supplement-hurt-your-weight-loss Mar. 18, 2019 (Mar. 18, 2019).
Amandean Natural Products, "Why Weight Watchers Fans Are Using Marine Collagen As Part of Their Daily Nutrition?", (https://www.amandean.com/blogs/news/marine-collagen-as-the-best-protein-to-pair-with-your-weight-watchers-program, Jan. 17, 2019). (Year: 2019), pp. 1-11.
Bundgaard, "Design of Prodrugs", Elsevier Science Publishers B.V. (Biomedical Division), Elsevier Amsterdam—New York—Oxford, 1985 (Year: 1985), 94 pages.
Silverman, "Prodrugs and Drug Delivery Systems", The Organic Chemistry of Drug Design and Drug Action, pp. 352-401, 1992), Chapter 8, ( Year: 1992), 25 pages.
USPTO, Restriction/Election Requirement dated Jun. 25, 2021 in U.S. Appl. No. 16/808,084.
USPTO, Non-Final Office Action dated Aug. 18, 2021 in U.S. Appl. No. 16/808,084.
USPTO, Final Office Action dated Nov. 30, 2021 in U.S. Appl. No. 16/808,084.
USPTO, Advisory Action dated Dec. 29, 2021 in U.S. Appl. No. 16/808,084.
USPTO, Notice of Allowance dated Mar. 8, 2022 in U.S. Appl. No. 16/808,084.
USPTO, Corrected Notice of Allowability dated Mar. 22, 2022 in U.S. Appl. No. 16/808,084.

(Continued)

*Primary Examiner* — Umamaheswari Ramachandran
(74) *Attorney, Agent, or Firm* — SNELL & WILMER L.L.P.

(57) ABSTRACT

An appetite suppressant composition may comprise at least one anorectic active ingredient; at least one of a nutritive substance, a cofactor; and optionally, an excipient. The anorectic active ingredient may comprise any one of phentermine, phendimetrazine, diethylpropion, naltrexone, and bupropion. The nutritive substance may comprise a protein source such as bovine collagen. The cofactor may comprise a chromium or selenium salt. In various embodiments, the compositions herein are provided in an oral capsule dosage form for GI-tract administration of the AAI. A method of suppressing appetite in individuals in need thereof are described.

12 Claims, No Drawings

(56) References Cited

OTHER PUBLICATIONS

CIPO; Office Action dated Jul. 14, 2022 in Canadian Application No. 3074541.
Amandean Wellness Center, "Why Weight Watchers Fans Are Using Marine Collagen As Part Of Their Daily Nutrition?", https://www.amandean.com/blogs/news/marinecollagenas-the-best-protein-to-pair-with-your-weight-watchers-program, Jan. 17, 2019 (Jan. 17, 2019).
CIPO, Notice of Allowance dated Mar. 13, 2023 in Canadian Application No. 3074541.
USPTO, Restriction/Election Requirement dated Sep. 26, 2023 in U.S. Appl. No. 18/171,822.
Kinman, Tricia ."About Sublingual and Buccal Medication Administration." Healthline, Jun. 6, 2017, https://www.healthline.com/health/sublingual-and-buccal-medication-administration. (Year: 2017), pp. 1-2.
Gonzales, Sarah. "Combining Phentermine with Other Supplements." PhenOnline, Oct. 5, 2022, https://phenonline.com/blog/combining-phentermine-with-other-supplements/. (Year: 2022), pp. 1-6.
drugs.com. "Nitroglycerin Lingual Spray: Package Insert." https://www.drugs.com/pro/nitroglycerin-lingual-spray.html. Last updated Feb. 5, 2023 (Year: 2023), 20 pages.
Evolvent. "Table of Viscosities"; https://oilviscositychart.com/learn/viscosity-list.php. Accessed Oct. 16, 2023. (Year: 2023), pp. 1-17.
NHR Organic Oils. "Certificate of Analysis Sheet: Organic MCT oil"; https://www.nhrorganicoils.com/uploads/certs/MCT%20CofA%20110718-17.pdf. Accessed Oct. 16, 2023 (Year: 2018), 1 page.
USPTO, Non-Final Office Action dated Oct. 23, 2023 in U.S. Appl. No. 18/171,822.

\* cited by examiner

APPETITE SUPPRESSANT COMPOSITIONS AND METHODS THEREOF

CROSS-REFERENCE TO RELATED APPLICATIONS

This application is a continuation of, claims priority to and the benefit of, U.S. application Ser. No. 16/808,084, filed Mar. 3, 2020 and entitled "Appetite Suppressant Compositions and Methods Thereof," (now U.S. Pat. No. 11,344, 556), the disclosure of which is incorporated herein by reference in its entirety for all purposes.

FIELD

This disclosure generally relates to pharmaceutical compositions, and more specifically, to orally administered appetite suppressant compositions and methods thereof.

BACKGROUND

Individuals from wealthy industrialized countries are increasingly obsessed by health and beauty. These individuals help fuel a multi-billion dollar market for OTC diet products, medically assisted weight loss such as prescription drugs and bariatric surgery, cosmetic surgery and cosmetics and anti-aging treatments. Some individuals find difficulty maintaining proper diet and exercise regiment, and are often turning to formulations and programs promoting rapid weight loss and body sculpting.

In the United States, an alarming percentage of the population is obese, yet the requirements for gastric bypass surgery remains that one be medically diagnosed obese. Others may find the surgery to not be worth the risk.

In view of these and other personal and physiological challenges in achieving and managing a healthy weight, new weight management compositions and health programs are still needed.

SUMMARY

In various embodiments, new appetite suppressant compositions are described. In various embodiments, appetite suppressant compositions are compounded in a dosage form for oral administration.

In various embodiments, new appetite suppressant compositions comprise an immediate release oral dosage form or a controlled release oral dosage form.

In various embodiments, new appetite suppressant compositions comprise an immediate release capsule oral dosage form.

In various embodiments, new appetite suppressant compositions comprise a controlled release capsule oral dosage form.

In various embodiments, an appetite suppressant composition comprises at least one anorectic active ingredient; at least one of a nutritive substance, a cofactor; and optionally, an excipient.

In various embodiments, the anorectic active ingredient is selected from the group consisting of diethylpropion, amphetamine, benfluorex, bupropion, butanolide, caffeine, cathine, cetilistat, clobenzorex, D-fenfluramine, racemic-fenfluramine, ephedrine, etilamfetamine, exenatide, FG-7142 (diazepine inverse agonist), higenamine, liraglutide, lorcaserin, mazindol, mefenorex, metformin, methamphetamine, naltrexone, nicotine, orlistat, phenmetrazine, phendimetrazine, phentermine, phenylpropanolamine, pramlinatide, pseudoephedrine, pyroglutamyl-histidyl-glycine, rimonabant, semaglutide, sibutramine, topiramate, yohimbine, pro-drugs thereof, pharmaceutically acceptable salts thereof, and mixtures thereof.

In various embodiments, the nutritive substance is selected from the group consisting of a dried *Spirulina* algal species biomass powder, a dried *Chlorella* algal species biomass powder, a hydrolyzed powdered bovine or fish collagen, a bovine or porcine gelatin powder, egg albumin powder, calcium caseinate powder, powdered milk protein concentrate, whey protein isolate powder, yellow pea protein isolate, and mixtures thereof.

In various embodiments, the cofactor is selected from the group consisting of calcium acetate, calcium ascorbate, calcium citrate, calcium gluconate, calcium nicotinate, calcium picolinate, chromium acetate, chromium ascorbate, chromium citrate, chromium gluconate, chromium nicotinate, chromium picolinate, copper acetate, copper ascorbate, copper citrate, copper gluconate, copper nicotinate, copper picolinate, magnesium acetate, magnesium ascorbate, magnesium citrate, magnesium gluconate, magnesium nicotinate, magnesium picolinate, manganese acetate, manganese ascorbate, manganese citrate, manganese gluconate, manganese nicotinate, manganese picolinate, potassium acetate, potassium ascorbate, potassium citrate, potassium gluconate, potassium nicotinate, potassium picolinate, selenium acetate, selenium ascorbate, selenium citrate, selenium gluconate, selenium nicotinate, selenium picolinate, zinc acetate, zinc ascorbate, zinc citrate, zinc gluconate, zinc nicotinate, zinc picolinate, and mixtures thereof.

In various aspects of an appetite suppressant composition, the anorectic active ingredient comprises phendimetrazine tartrate, the nutritive substance comprises hydrolyzed powdered bovine or fish collagen, and the cofactor comprises calcium picolinate, chromium picolinate, copper picolinate, magnesium picolinate, manganese picolinate, selenium picolinate, or zinc picolinate. A pharmaceutical dosage form for oral administration comprises a capsule and this composition enclosed therein.

In various aspects of an appetite suppressant composition, the anorectic active ingredient comprises diethylpropion-HCl with 1% tartaric acid, the nutritive substance comprises hydrolyzed powdered bovine or fish collagen, and the cofactor comprises calcium picolinate, chromium picolinate, copper picolinate, magnesium picolinate, manganese picolinate, selenium picolinate, or zinc picolinate. A pharmaceutical dosage form for oral administration comprises a capsule and this composition enclosed therein.

In various embodiments, an appetite suppressant composition consists essentially of from 12.0 wt. % to 18.0 wt. % phendimetrazine tartrate; from 80.0 wt. % to 90.0 wt. % bovine collagen; and from 0.05 wt. % to 0.10 wt. % chromium picolinate. A pharmaceutical dosage form for oral administration comprises a capsule and this composition enclosed therein.

In various embodiments, a method of suppressing appetite in an individual comprises orally administering to the individual in need thereof a therapeutically effective amount of an appetite suppressant composition consisting essentially of from 12.0 wt. % to 18.0 wt. % phendimetrazine tartrate; from 80.0 wt. % to 90.0 wt. % bovine collagen; and from 0.05 wt. % to 0.10 wt. % chromium picolinate. An appetite suppressant dosage form consists essentially of 250 mg to 300 mg of this composition as a loose powder and a dissolvable capsule encapsulating said composition.

In various embodiments, the therapeutically effective amount comprises orally administering up to 210 mg per day of the phendimetrazine tartrate.

In various embodiments, the individual in need thereof is diagnosed overweight and obese.

In various embodiments, an appetite suppressant composition consists essentially of from 6.0 wt. % to 12.0 wt. % diethylpropion-HCl, said diethylpropion-HCl including 1% tartaric acid; from 50.0 wt. % to 58.0 wt. % bovine collagen; and from 0.05 wt. % to 0.10 wt. % chromium picolinate. A pharmaceutical dosage form for oral administration comprises a capsule and this composition enclosed therein.

In various embodiments, a method of suppressing appetite in an individual comprises orally administering to the individual in need thereof a therapeutically effective amount of an appetite suppressant composition consisting essentially of from 6.0 wt. % to 12.0 wt. % diethylpropion-HCl, said diethylpropion-HCl including 1% tartaric acid; from 50.0 wt. % to 58.0 wt. % bovine collagen; and from 0.05 wt. % to 0.10 wt. % chromium picolinate. An appetite suppressant dosage form consists essentially of 250 mg to 300 mg of this composition as a loose powder and a dissolvable capsule encapsulating said composition.

In various embodiments, the therapeutically effective amount comprises orally administering up to 150 mg per day of the diethylpropion-HCl.

In various embodiments, the individual in need thereof is diagnosed overweight and obese.

DETAILED DESCRIPTION

The detailed description of exemplary embodiments refers to the accompanying drawings, which show exemplary embodiments by way of illustration and best mode. While these exemplary embodiments are described in enough detail to enable those skilled in the art to practice the invention, other embodiments may be realized, and logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Appetite suppressant compositions comprising an appetite suppressant pharmaceutical active, (e.g., an anorectic active ingredient, or "AAI") are described. In various embodiments, an appetite suppressant composition in accordance with the present disclosure comprises: at least one AAI; and any one of or combination of nutritive substances, controlled drug release agents ("CDRAs"), cofactors, excipients, and/or fillers.

Definitions

As used herein, the terms "anorectic," or "appetite suppressant," or "anorectic pharmaceutical active," or "anorectic AI" (AI=active ingredient), or most simply, the acronym "AAI," refer to any chemical substance now known or yet to be discovered that is capable of suppressing the feeling of hunger and/or the craving for food in an individual, regardless if the chemical substance is currently registered with a regulatory agency, such as the United States Food & Drug Administration (FDA) or not. For example, an AAI for use herein may comprise a chemical newly synthesized in a research laboratory, or a natural product just having been isolated, and not yet presented to any regulatory agency which might never be registered. Included in the broad class of known AAIs are the very familiar alkaloids caffeine and nicotine. Some AAIs mentioned for use herein may have additional pharmacological effects besides appetite suppression, e.g., anti-obesity, or might indirectly provide appetite suppression as a consequence or artifact of a primary pharmacological effect (e.g., glucose production controlled by diabetes medications). Current regulatory status, including withdrawal from registered use, is not considered since prior regulatory issues could have been related to physical dosage forms or administration routes and practices that are not within the scope of the present disclosure.

In various embodiments, AAIs that find use in the present appetite suppressant compositions in accordance with the present disclosure include, but are not limited to, amfepramone (diethylpropion), amphetamine and analogs thereof, benfluorex, bupropion, butanolide, caffeine, cathine, cetilistat, clobenzorex, dexfenfluramine (D-fenfluramine), ephedrine, etilamfetamine, exenatide, racemic-fenfluramine, FG-7142, higenamine, liraglutide, lorcaserin, mazindol, mefenorex, metformin, methamphetamine and analogs thereof, naltrexone, nicotine, orlistat, phenmetrazine, phendimetrazine, phentermine, phenylpropanolamine, pramlinatide, pseudoephedrine, pyroglutamyl-histidyl-glycine, rimonabant, semaglutide, sibutramine, topiramate, yohimbine, pro-drugs thereof, pharmaceutically acceptable salts thereof, and combinations thereof. Any of these AAIs may be commercially obtained and pharmaceutically administered as a salt, e.g., a hydrochloride salt or a tartrate salt. For simplicity, reference is made to the active without the -HCl or -tartrate suffix designation. In various embodiments, whole plant or fungal material (e.g., ephedra (Ma Huang), bitter melon, maitake, purslane, tea), or any plant, root, bark, tree or flower extract, may be used as an AAI herein, recognizing that the appetite suppressant effect may be more of any one of a homeopathic effect, prophylactic effect, sensory effect, placebo effect, or psychological effect rather than a recognizable physiological effect describable by biochemical pathways.

AAIs for use herein may comprise drugs characterizable or otherwise known as stimulants, antidiabetic agents, glucose regulating agents, thyroid hormones, thyroid drugs, parathyroid drugs, vitamins, antihyperlipidemic agents, cardiac drugs, respiratory drugs, nasal decongestants, gastrointestinal drugs, amphetamines, anorexiants, antirheumatic agents, anti-gout agents, migraine drugs, sedatives, hypnotics, antianxiety drugs, anticonvulsants, antidepressants, antipsychotic agents, psychotherapeutic drugs, antimicrobials, antifungals, sulfonamides, antimalaria drugs, antituberculotic drugs, amebicides, antiviral agents, anti-infectives, leprostatics, antihelmintics, antihistamines, antimetabolites, anticholinergics, steroidal anti-inflammatories, anesthetics, antiplatelet drugs, NSAIDs, ace inhibitors, calcium channel blockers, alpha-blockers, muscle relaxers, antihypertensives, vasodilators, diuretics, antiemetics, sex hormones, pituitary hormones, analgesics, uterine hormones, and adrenal steroid inhibitors. Such drugs might have a primary known physiological use, like a stimulant, but also a secondary appetite suppressant effect.

As used herein, the term "cofactor" refers to a non-protein substance that associates with an enzyme in order for the enzyme to function in vivo. In general, enzyme cofactors include both inorganic ions, such as metal cations, and organic molecules including a number of vitamins and nucleotides. For use herein, metal cation cofactors include, but are not limited to, $Ba^{2+}$, $Ce^{3+}$, $Cd^{2+}$, $Co^{2+}$, $Co^{3+}$, $Cr^{2+}$, $Cr^{3+}$, $Cr^{6+}$, $Cu^{1+}$, $Cu^{2+}$, $Fe^{2+}$, $Fe^{3+}$, $K^{+1}$, $La^{3+}$, $Mg^{2+}$, $Mn^{+2}$, $Mn^{3+}$, $Mo^{2+}$, $Mo^{3+}$, $Mo^{4+}$, $Mo^{+5}$, $Ni^{1+}$, $Ni^{2+}$, $Se^{2+}$, $Zn^{2+}$, iron-sulfur clusters (e.g., $Fe_2S_2$ and $Fe_4S_2O_2$ iron-sulfur-oxygen cluster), and combinations thereof. The anion for any of these and other metal cation cofactors can be any inorganic or organic anion, such as a halide, carbonate, phosphate, pyrophosphate, tripolyphosphate, sulfate, sulfide, or a carboxylate (nicotinic acid, isonicotinic acid, acetate, etc.), or a bidentate, tridentate, tetradentate, or other chelating or coordination agent, such as ascorbic acid, citric acid, dimercaprol, gluconic acid, nicotinamide, oxalic acid, 1,10-phenanthroline, picolinic acid, 2-(2'-pyridyl)imidazole, 2-(2'-pyridyl)benzimidazole, ethylenediamine, ethylenediaminetetraacetic acid (EDTA), acetylacetonate, and combinations thereof. For oral administration and GI tract bioavailability, it is more common to use an organic anion (e.g., acetate, nicotinate, etc.) or a bidentate, tridentate, tetradentate, or other complexed metal cation (e.g., gluconate, citrate, picolinate, etc.) for a cofactor rather than an inorganic anion (e.g., chloride, sulfate, etc.) to provide the metal cation active portion of the cofactor. In some instances, both the cation and the anion can be active physiological agents, (e.g., nicotinate salts, since nicotinic acid is niacin, or vitamin B3). Further, in certain complexes, one or more coordination compounds and inorganic anions might associate with a single metal cation, (e.g., bis-phenanthroline Cr(III) complexes can include two chlorine atoms bonded to the chromium, and $Cl^-$ as a counterion to the 1+ charged complex). In specific embodiments, cofactors for use in the compositions of the present disclosure include calcium acetate, calcium ascorbate, calcium citrate, calcium gluconate, calcium nicotinate, calcium picolinate, chromium acetate, chromium ascorbate, chromium citrate, chromium gluconate, chromium nicotinate, chromium picolinate, copper acetate, copper ascorbate, copper citrate, copper gluconate, copper nicotinate, copper picolinate, magnesium acetate, magnesium ascorbate, magnesium citrate, magnesium gluconate, magnesium nicotinate, magnesium picolinate, manganese acetate, manganese ascorbate, manganese citrate, manganese gluconate, manganese nicotinate, manganese picolinate, potassium acetate, potassium ascorbate, potassium citrate, potassium gluconate, potassium nicotinate, potassium picolinate, selenium acetate, selenium ascorbate, selenium citrate, selenium gluconate, selenium nicotinate, selenium picolinate, zinc acetate, zinc ascorbate, zinc citrate, zinc gluconate, zinc nicotinate, zinc picolinate, and mixtures thereof.

For use herein, organic cofactors include, but are not limited to, vitamins A, C, B1, B2, B3, B6, B12, H and K, thiamine pyrophosphate, NADH, NAD+, NADP+, FAD, FADH, pyridoxal phosphate, methylcobalamine, cobalamine, biotin, coenzymes A, B, M and Q10 (ubiquinone), folic acid, tetrahydrofolic acid, menaquinone, ascorbic acid, flavin mononucleotide, coenzyme F420, adenosine 5'-monophosphate, ADP, ATP, cytidine triphosphate, glutathione, lipoamide, β-carotene, (6R)-5,10-methylenetetrahydrofolate, (6R)-5,10-methylenetetrahydrofolic acid, (6S)-5,6,7,8-tetrahydrofolate, (6S)-5,6,7,8-tetrahydrofolic acid, (R)-lipoate, (R)-lipoic acid, 1,4 benzoquinone, 3'-hydroxyechinenone 5,6,7,8-tetrahydropteridine, 5-hydroxy-benzimidazolylcob (I)amide, 5-hydroxy-benzimidazolyl-cob(I)amide, 7-dimethyl-8-(1-D-ribityl)lumazine, 6,7-dimethyl-8-(1-D-ribityl)lumazine, 6-decylubiquinone, 6-hydroxy-FAD, myo-inositol hexakisphosphate, S-adenosyl-L-homocysteine, S-adenosyl-L-methionine zwitterion, S-adenosyl-L-methionine zwitterion, L-ascorbate, L-ascorbic acid, ammonium cation ($NH_4^+$), bacillithiol, biotinate, bis(molybdopterin)tungsten, chlorophyll a, chlorophyll b, cobamamide, corrin, corrinoid, decylplastoquinone, dehydro-D-arabinono-1,4-lactone, dihydrogen vanadate, dihydrolipoamide, dipyrromethene, dipyrromethene, divinyl chlorophyll a, divinyl chlorophyll b, echinenone, Fe-coproporphyrin III, ferriheme a, ferroheme b, ferroheme cmethanofuran, molybdopterin, various nucleotide sugars, 3'-phosphoadenosine-5'-phosphosulfate, quinone, pyrroloquinoline quinone, tetrahydrobiopterin, tetrahydromethylbioterin, prodrugs thereof, pharmaceutically acceptable salts thereof, and combinations thereof.

As used herein, the term "prodrug" refers to an AAI that is prepared in an inactive form that is converted to an active form within the body or cells thereof by the action of endogenous enzymes or other chemicals and/or conditions. In various embodiments, a prodrug-AAI is compounded into a loose powder composition and loaded into capsules for oral administration, whereby the prodrug-AAI is converted to the active AAI in the GI tract of the individual.

As used herein, the term "controlled drug release agent" (or more simply, the acronym "CDRA"), refers to an organic substance capable of agglomerating around an AAI so as to slow down the bioavailability of the AAI in the GI tract. In various embodiments, an AAI may be intimately mixed with a CDRA in a powder composition for capsule delivery. When the capsule dissolves in the stomach, the CDRA swells with water, physically trapping the AAI (and other active ingredients) until the GI tract, e.g., catalyzed by acidity and temperature in the gut, can break down the CDRA. In various embodiments, CDRAs for use herein comprise certain particle sizes, and in some instances, nanoparticles. In various embodiments, CDRAs for use herein comprise natural, semisynthetic and synthetic hydrophilic polymers capable of gelling and/or swelling. In various embodiments, CDRAs for use herein comprise hydrogel materials, also known as polymer hydrogels or PHGs. CDRAs for biological applications, such as herein, are generally polysaccharides or polypeptides. Combinations of hydrogels may be used to create "core-shell" composite hydrogels. Distinction is made between a CDRA for use to slow down active drug release and a disintegrant for use in speeding up drug release, even though in a formal sense, speeding up drug active delivery is still a form of "controlling" drug release. Attempt is made herein to categorize disintegrants with "excipients" and to keep CDRAs in a separate category of ingredients.

CDRAs for use herein include, but are not limited to, agar, agarose, albumin, alginate, casein, chitin, chondroitin, dextrin, fibroin, fucoidans, galactans, gellan, guar, scleroglucan, pullulan, xyloglucan, pectin, xanthan, psyllium, silica gel, fumed silica, magnesium aluminum silicates, clay, bentonite, hectorite, mesoporous silica, cellulose, cellulose acetate, hyaluronan, various elastin-like polypeptides, O-cyclodextrin, collagen, gelatin, chitosan, carrageenan, polylactic acid, polyglycolic acid, poly(lactic-glycolic acid) (PLGA), poly (2-hydroxyethyl methacrylate), poly(2-hydroxypropyl methacrylate), poly(acrylic acid), carboxymethyl cellulose, carboxyethyl cellulose, hydroxyethyl cellulose, hydrophobically-modified hydroxyethyl cellulose, hydroxypropyl cellulose, hydroxypropyl methyl cellulose, methyl cellulose, ethyl cellulose, microcrystalline cellulose, nitrocellulose, polyvinyl alcohol, polyvinylpyrrolidone, polyvinylmethacrylate, carboxyvinyl polymers, polyvinylacetate, polyvinyl co-polymers, various starches, modified starches, and combinations thereof. See, S. M. Fijul Kabir, et al., "Cellulose-based hydrogel materials: chemistry, properties and their prospective applications,"*Prog. Biomater.*, 7, 153-174 (2018).

As used herein, the term "immediate release" refers to a pharmaceutical dosage form designed to fall apart, dissolve, or otherwise disintegrate as quickly as possible. Typically, a dosage form for immediate release will be an oral dosage form, such as a tablet for sublingual drug administration or a capsule for swallowing with subsequent GI drug delivery. Capsule dosage forms may be designed for immediate drug release by changes to either the capsule shell, or the powder fill composition, or both. For example, hard capsule shells may be laser-drilled with holes that allow entry of water in the gut. In other examples, one or more disintegrating agents (called "disintegrants") may be added into the powder fill composition of a capsule, or into the capsule shell itself. In various embodiments, immediate release may also be coupled with increased GI absorption, and in those instances an intestinal permeation enhancer may be included in an immediate release composition so that there is not only rapid dissolution of the capsule, there is also rapid intestinal absorption. In various embodiments, a standard gel cap or powder filled hard gelatin capsule may provide immediate release in the gut simply in response to physiological conditions of heat and acid in the stomach, sufficiently capable of dissolving a gelatin shell in due course. Immediate release tends to be the opposite of controlled release or sustained release.

As used herein, the term "nutritive" refers to any substance providing caloric or other nutritional value to an individual, including any substances from the classic food groups of protein, carbohydrate, and fat. A nutritive for purposes herein may also include nutritive fiber, but a distinction will be made between nutritive fiber and fibrous materials that swell into hydrogels for controlled drug release purposes, such as cellulosic materials. In other words, a cellulosic in an appetite suppressant composition herein is likely present in the composition for sustained AAI release purposes rather than for supplying digestive fiber. Another example is psyllium, a well-known digestive fiber, but a material that also acts as a CRDA because of its ability to swell in the gut and occlude other materials. In various embodiments, a nutritive may comprise a nutritive filler. Said another way, a nutritive such as a protein powder may be used in "quantity sufficient" (q.s.) to fill in the remainder of a composition totally 100 wt. %.

As used herein, the term "protein source" refers to an organic substance or mixture that provides a moderate to a high level of protein, shorter chain peptides, and/or amino acids (e.g., at least about 60 wt. % peptide materials) based on the total weight of the protein material. In various embodiments, a protein source may be similar if not identical to substances used in protein shakes in the health and fitness industry, and may be animal or plant derived, including aquatic plant. In various embodiments, a protein source for use herein may be hydrolyzed so that it can be intestinally absorbed more easily than the parent protein prior to hydrolysis. Protein sources for use herein include, but are not limited to, whey, casein, lectin, collagen, egg protein, pea protein, hemp protein, brown rice protein, alfalfa, chia, flax, artichoke, quinoa, a *Spirulina* algal species, a *Chlorella* algal species, a Schizochytrium algal species, a *Laminaria* algal species, an Ulva algal species, an *Arthrospira* algal species, a *Porphyridium* algal species, a *Haematococcus* algal species, and combinations thereof. For any of the plant and animal sources of protein, the raw animal or plant material or isolated protein may be left natural or hydrolyzed, and then dried into a powder. For the algal species, the protein source may comprise the algal biomass itself (e.g., plant matter simply squeezed out, dried or spray dried, and powdered) or the protein source may be isolated and/or hydrolyzed proteins extracted from the algal sources. See, S. Bleakley, et al., "Algal Proteins: Extraction, Application, and Challenges Concerning Production," *Foods,* 6(5), 33 (2017).

As used herein, the term "filler" refers to non-nutritive materials that may be added in quantity sufficient to complete a formula to "100%" total. In various embodiments, appetite suppressant compositions comprise a number of pharmacologically active substances, such as AAIs, nutritive substances, CRDAs, and cofactors, with the remainder comprising inert filler. In other embodiments, compositions herein comprise sufficient nutritive substances, like protein sources, such that inert fillers for weight and bulk are not needed. Fillers increase weight, but typically do not contribute to any pharmacological effect. Pharmaceutically acceptable inert fillers are known to the pharmaceutical arts, and include such substances as monosaccharides and disaccharides, (mannitol, lactose, dextrose) carbonates (calcium carbonate), phosphates, (calcium phosphate), and sulfates (calcium sulfate). For an exhaustive listing of pharmaceutically acceptable fillers, see "Handbook of Pharmaceutical Excipients, $6^{th}$ Edition, R. C Rowe, et al., editors, Pharmaceutical Press, London, 2009.

As used herein, the term "excipient" refers to additional functional ingredients in an appetite suppressant composition, and thus distinct from inert filler. Excipient refers to those ingredients that although functional, play a minor role in the composition. These ingredients typically include disintegrants, colors, flavorants, sweeteners, and preservatives.

As used herein, the term "composition" takes on the ordinary meaning in formulation chemistry as a combination of ingredients. In various embodiments, a composition is designed to adopt a particular physical form, or at least be amenable to physical change into a desired physical form, which may be the dosage form for a particular treatment regimen. Typically, a composition is made homogeneous by mixing or blending, although not all liquid compositions are colorless and transparent and not all powder compositions are white and perfectly granular. Compositions comprising an emulsion, dispersion or suspension may be homogeneous because the droplets or particles are evenly spread in a carrier. So, for example, a composition herein may be in the form of a thin liquid (having a viscosity at or near that of water), a viscous liquid (having a liquid of viscosity greater than water), a paste, a cream, a jelly, a gel, or a powder. Ingredients for a composition herein are generally shown "as added," meaning there is a possibility for one or more chemical reactions between ingredients once the ingredients are mixed together, such as into a common carrier. One skilled in the art of formulation chemistry can recognize whether ingredients might react in a mixture. These reactions can include neutralization (e.g., between acid and alkali ingredients), mixed micelle formation (mixed surfactants in liquid systems) or other encapsulation phenomena, hydrolysis, and so forth. In various embodiments, a composition herein comprises a blended powder that can be packed into capsules for oral administration. In some instances, a composition may take into consideration an outer encasing when that material is also included in the administration of the composition to an individual. For example, a gelatin capsule may be included in the listing of ingredients for a composition, or perhaps just the ingredients of the contents of the capsule may be listed. In various embodiments, ingredients in a composition are listed in "weight percent," (i.e., "wt. %"), based on the total weight of the composition. For example, 100 milligrams of a composition comprising 40 mg A and 60 mg B may be recited as "40 wt. % A and 60 wt. % B, based on the total weight of the composition," which necessarily totals to "100 wt. %." The actual weight amounts, (e.g., milligrams or grams) generally refers to amounts added for a particular batch size, (e.g., a batch size of powder usable to fill 100 capsules).

As used herein, the term "dosage form" takes on its ordinary meaning in the pharmaceutical arts as the physical form of a composition designed for a particular administration route. For example, dosage forms include, but are not limited to, injectables, infusible liquids, nasal sprays, nasal gels, topicals such as transdermal creams, ointments and patches, loose powders, tablets, sublingual tabs, capsules, lozenges, syrups, vapors, and so forth. In various embodiments, compositions of interest herein comprise powders, and the dosage form comprises a capsule comprising the powdered composition encased or "encapsulated" in the capsule or a table comprising the powdered composition compressed into a shape for oral swallowing or sublingual dissolution.

As used herein, the term "capsule" generally refers to a one or two piece enclosure for a loose powder, which can be swallowed for oral administration of the powder contents of the capsule, or a soft-shell for a liquid composition, otherwise known as a "gel cap"). In general, "soft" capsules for liquids are one piece, whereas "hard" capsules for powders are two piece. In some instances, the capsule is said to "encapsulate" the powder contained therein, which can be confusing because the term "encapsulation" is often used, perhaps more correctly used to describe a microscale or nanoscale phenomenon rather than describing something macroscopic like a drug dosage form. In various embodiments, capsules for use herein are hard, stable two piece shells, or enclosures, capable of stably holding a powder fill, and capable of disintegrating in the gastrointestinal track of an individual. Capsules for use herein may comprise any combination of animal gelatin, plant polysaccharides (carrageenan, etc.), or starch or derivatives thereof. In some instances, capsules may further comprise plasticizers, colors, preservatives, disintegrants, lubricants, and various surface treatments such as laser perforations. In various embodiments, a capsule may be transparent so that the contents are visible, or entirely opaque to obscure the contents. In various embodiments, the rate of delivery of an AAI from a two piece hard capsule having a powder fill may be controlled by any combination of ingredients in the powder fill and ingredients or design configurations of the capsule itself. For example, a capsule intended for immediate release of an active drug may comprise a micronized powder fill in combination with a laser perforated capsule having disintegrants incorporated in the capsule material. On the other hand, a capsule intended for slow or controlled release may have a powder fill configured with a CDRA, like a cellulosic, to coagulate in the gut, slowing active bioavailability, in combination with a slower dissolving capsule shell, such as one comprising a plasticizer. In various embodiments, an AAI or other bioactive substance may be embedded in the capsule material.

Two piece hard capsules for use herein can be characterized by a size scale that includes size 5, 4, 3, 2, 1, 0, 0E, 00, 000, 13, 12, 12e1, 11, 10, 7 and Su07, (in increasing order of physical dimensions and internal volume when assembled). Typically, only the capsule sizes from 5 (11.1 mm×4.91 mm, 0.13 mL volume) up through about 000 (26.14 mm×9.91 mm, 1.36 mL) would be practical for human oral consumption, and digestive tract (enteral) route of administration.

As used herein, the term "subject" or the phrase "a subject in need thereof" refers to any human or non-human animal requiring or desirous of a pharmacological change. For example, a subject in need thereof may be a human patient clinically diagnosed with obesity, an eating disorder, or health issues relating to poor BMI, fat along the waistline, diet in general, or lack of exercise. In various embodiments, the subject in need thereof is a person desirous of a reduced appetite such that they can lose weight and/or improve health. Most importantly, a subject in need thereof can be any human in good health, but desirous of maintaining good health. In other words, the subject in need thereof may be desirous of a prophylactic regimen, like taking daily vitamins. The subject in need thereof may have the outward appearance of a person of average weight for their age, height and gender, but desirous of maintaining that weight, and thus desirous of curbing appetite in general.

As used herein, the term "treatment" of a subject (e.g., a human) is any type of intervention used in an attempt to alter the natural course of the subject. Treatment includes, but is not limited to, administration of an appetite suppressant composition in accordance with the present disclosure, and may be performed either prophylactically or subsequent to the initiation of a pathologic event or diagnosis of a physical issue, such as obesity. Also included are "prophylactic" treatments, which can be directed to reducing the rate of progression of obesity or condition being treated, delaying the onset of weight or condition, or reducing the severity of its onset. "Treatment" or "prophylaxis" does not necessarily indicate complete eradication, cure, or prevention of a disease or condition, or associated symptoms thereof. Treatment may also be entirely for cosmetic reasons, such as where an individual has not received any diagnosis of having a weight issue or a need for weight loss, but for whom obtaining or maintaining a slim figure is desirous for some reason, such as to succeed in a particular profession.

As used herein, the term "therapeutically effective amount" refers to a minimum dosage of a composition in accordance with the present disclosure that provides a desired effect. Therefore, a therapeutically effective amount varies by subject, dosage form, concentration of one or more AAIs in the composition, and the ultimate results desired. For example, a therapeutically effective amount of a capsule disclosed herein to treat an overweight individual might be on the order of three (3) 150 mg capsules per day. In other examples, a therapeutically effective amount of a capsule disclosed herein to treat a morbidly obese individual might be on the order of six (6) 150 mg capsules per day.

As used herein, the term "prophylactically effective amount" refers to a minimum dosage of an appetite suppressant composition in accordance with the present disclosure that provides maintenance of a desired level of health. Therefore, a prophylactically effective amount varies by subject, (particularly age, gender, height, weight, and current health habits and any ongoing health issues), dosage form, concentration of one or more AAIs in a composition, and the results desired. For example, a prophylactically effective amount of a capsule composition disclosed herein to promote general health in a male of fairly average weight who exercises moderately may be one (1) 150 mg capsule per day, such as before dinner or when that individual fears overeating.

As used herein, the term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more appetite suppressant compositions in accordance with the present disclosure to produce or cause a greater physiological response (i.e., downstream effects) in a cell or in a subject relative to the response caused by either no appetite suppressant composition or a control compound. Relevant physiological or cellular responses (in vivo or in vitro) upon administration of appetite suppressant compositions will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7. 1.8), the amount produced by no appetite suppressant composition (the absence of a bioactive agent) or a control compound. The term "reduce" or "inhibit" may relate generally to the ability of one or more appetite suppressant compositions to "decrease" a relevant physiological or cellular response, such as a symptom of a disease like obesity or a condition like excessive weight described herein, as measured according to routine techniques in the diagnostic art. Relevant physiological or cellular responses (in vivo or in vitro) will be apparent to persons skilled in the art, and may include reductions in the symptoms or pathology of a disease such as obesity and related issues like inflammation or pain. A "decrease" in a response may be "statistically significant" as compared to the response produced by no appetite suppressant composition or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As used herein, the term "naturally occurring" refers to an AAI obtained in its active form from nature. In various embodiments, it is possible that an AAI is not identifiable or characterizable in a natural form. For example, an AAI for use herein may be a dried and powdered plant leaf, containing hundreds of structurally complex organic substances, but which acts as an AAI even though there is no way to conclusively say what substance or substances in the complex mixture is providing the observed physiological effect, i.e., appetite suppression. In other words, the true active or actives in a natural material, like a ground leaf, may never be known, but for simplicity, the natural material may be referred to as an AAI because of the effect it can elicit.

As used herein, the term "semisynthetic" refers to an AAI obtained by one or more reactions in synthetic organic chemistry, beginning with a naturally occurring substance. In other words, a naturally occurring substance may need to undergo one or more synthetic steps in a laboratory or chemical process plant to be ultimately useful as an AAI for a composition herein.

As used herein, the term "synthetic" refers to an AAI that is made entirely by organic synthesis, such as through a linear or convergent strategy, possibly involving asymmetric synthesis as needed to obtain a specific enantiomer of an AAI, such as directing formation of a chiral center using a chiral reagent.

As used herein, the term "approximately" in reference to amounts refers to plus or minus 5% of the value given, such as wt. %. The term "about," a in reference to amounts refers to plus or minus 10% of the value given, such as wt. %.

General Embodiments

In various embodiments, an appetite suppressant composition in accordance with the present disclosure comprises: at least one AAI; and any one or combination of a nutritive substance, a CDRA, a cofactor, an excipient, and/or a filler. In various embodiments, the AAI is selected from the group consisting of phentermine, diethylpropion, phendimetrazine, bupropion, naltrexone, prodrugs thereof, pharmaceutically acceptable salts thereof, and combinations thereof. In various embodiments, the nutritive substance comprises a protein source. In various embodiments, the CDRA comprises a cellulosic. In various embodiments, the appetite suppressant composition is in the physical form of a loose powder for filling capsules, and wherein the dosage form to administer the composition comprises an extended release capsule. In various embodiments, the CDRA component is absent in the loose powder composition, and the dosage form to administer the composition comprises an immediate release capsule.

(I) In various embodiments, an appetite suppressant composition in accordance with the present disclosure comprises: at least one AAI; a nutritive substance; a CDRA; a cofactor; and optional excipients. In various embodiments, the AAI is selected from the group consisting of phentermine, diethylpropion, phendimetrazine, bupropion, naltrexone, prodrugs thereof, pharmaceutically acceptable salts thereof, and combinations thereof. In various embodiments, the nutritive substance comprises a protein source. In various embodiments, the CDRA comprises a cellulosic. In various embodiments, the appetite suppressant composition is in the physical form of a loose powder for filling capsules, and wherein the dosage form to administer the composition comprises an extended release capsule.

(II) In various embodiments, an appetite suppressant composition in accordance with the present disclosure comprises: at least one AAI; a CDRA; and optional excipients. In various embodiments, the AAI is selected from the group consisting of v In various embodiments, the CDRA comprises a cellulosic. In various embodiments, the appetite suppressant composition is in the physical form of a loose powder for filling capsules, and wherein the dosage form to administer the composition comprises an extended release capsule.

(III) In various embodiments, an appetite suppressant composition in accordance with the present disclosure comprises: at least one AAI; a nutritive substance; a cofactor; and optional excipients. In various embodiments, the AAI is selected from the group consisting of phentermine, diethylpropion, phendimetrazine, bupropion, naltrexone, and combinations thereof. In various embodiments, the appetite suppressant composition is in the physical form of a loose powder for filling capsules, and wherein the dosage form to administer the composition comprises an immediate release capsule.

In these general embodiments of appetite suppressant compositions, the at least one AAI is present (at a combined weight if more than one) from about 0.1 wt. % to about 10.0 wt. %, based on the total weight of the composition, and depending on the actual AAI chemical species used and the desired strength of the AAI(s) in the finished dosage form. In various embodiments, any AAI may be in the form of a pharmaceutically acceptable salt, such as the hydrochloride salt, or tartrate salt, or other salt to provide a more water soluble form.

In general embodiments of appetite suppressant compositions comprising a protein source as the nutritive substance, the protein source may be selected from the group consisting of a dried *Spirulina* algal species biomass powder having >about 60 wt. % protein (e.g., *S. platensis, S. maxima*), a dried *Chlorella* algal species biomass powder having >about 60 wt. % protein (e.g., *C. pyrenoidosa, C. vulgaris*), (available from Nanjing NutriHerb BioTech Co., LTD, Nanjing, China), a hydrolyzed powdered animal collagen (e.g., bovine or fish), a gelatin powder (e.g., bovine or porcine collagen that has been partially hydrolyzed), egg albumin powder, calcium caseinate powder, powdered milk protein concentrate (many of the above-mentioned animal derived protein raw material powders are available from Heathy Solutions, LLC, Scottsdale AZ, USA), whey protein isolate powder (from Antler Farms®, Hornby South, Christchurch, New Zealand), or a dried legume, grain, vegetable, nut or seed protein isolate or hydrosylate powder (from brown rice, lentils, yellow pea, or hemp seeds, particularly yellow pea protein isolate), available, e.g., from AXIOM Foods, Los Angeles, CA, USA. See, J. Y. Nehete, "Natural proteins: Sources, isolation, characterization and applications,"*Pharmacogn. Rev.*, 7(14) 107-116 (2013).

Table 1 sets forth these three general embodiments (I, II, III) in accordance with the present disclosure. The compositions are in the physical form of a loose powder, which can be loaded into capsules to provide dosage forms for oral administration. General embodiments I and II encompass the compositions for use in a controlled (extended) release dosage form, whereas general embodiment III encompasses the compositions for use in an immediate release dosage form. In any of the specific compositions under I, II, and III, the loose fill composition may be loaded into two-piece hard shell capsules. The capsule shell may be modified as necessary to be more appropriate for controlled release versus immediate release.

CDRA, like a cellulosic substance, and the nutritive substance, like a protein powder, can vary as necessary to make up the remainder of a capsule fill.

In various embodiments, the AAI is selected from the group consisting of phentermine, diethylpropion, phendimetrazine, bupropion, naltrexone, and combinations thereof. In various embodiments, the AAI consists of phentermine used on its own. In various embodiments, the AAI is phentermine-HCl. In various embodiments, consists of phendimetrazine used on its own. In various embodiments, the AAI is phendimetrazine tartrate. In various embodiments, the AAI is diethylpropion used on its own. In various embodiments, the AAI is diethylpropion HCl with 1% tartaric acid. In various embodiments, the AAI is a combination of naltrexone and bupropion. In various embodiments, the AAI is a mixture of naltrexone-HCl and bupropion-HCl.

In various embodiments, the appetite suppressant composition contain no inert filler, although recognizing a cellulosic CDRA is non-nutritive, and thus acts as a filler as discussed above. In other words, in certain variations, the only non-nutritive substance in an appetite suppressant composition in accordance with the present disclosure is the CDRA, such as if it is cellulosic and hence not digestible.

In various embodiments, an appetite suppressant composition in accordance with the present disclosure comprises any combination of optional excipients. In various embodiments, an appetite suppressant composition contains no excipients. In some instances, there is no taste to mask in a swallowed capsule, and perhaps no need for colorants, sweeteners or preservatives. Depending on the AAI, and whether a filled capsule is designed for extended release or immediate release, it may be necessary to include a flavorant.

In various embodiments, the optional one or more excipients include any one or combination of flavorant, sweetener, buffer (or acidic agent and/or alkali agent), colorant, disintegrant, intestinal permeation enhancer, stabilizer, preservative, or other pharmaceutically acceptable substance. Any of these materials not specifically mentioned herein may be found in "Handbook of Pharmaceutical Excipients, 6$^{th}$ Edition, R. C Rowe, et al., editors, Pharmaceutical Press,

TABLE 1

General Appetite Suppressant Compositions

| Ingredient (wt. %) | Compositions | | |
| --- | --- | --- | --- |
| | I | II | III |
| Anorectic Active Ingredient(s) (AAI) | 4 to 25 | 40 to 65 | 5 to 20 |
| Controlled Drug Release Agent (CDRA) | 40 to 50 | 35 to 60 | -0- |
| Nutritive Substance (e.g., a protein source) | 10 to 50 | -0- | 50 to 85 |
| Cofactor | 0.01 to 0.1 | -0- | 0.01 to 0.1 |
| Excipients (color, flavor, etc.) | 0 to 40 | 0 to 40 | 0 to 40 |
| Total | 100.00 wt. % | 100.00 wt. % | 100.00 wt. % |
| Physical Appearance | Loose powder | Loose powder | Loose powder |
| Use | Extended Release | Extended Release | Immediate Release |

In various embodiments, any combination of the at least one nutritive substance and the at least one CDRA may be used to bulk the composition "quantity sufficient" to 100% total. In other words, the AAI and the cofactor are likely to be the most important in a dosage regimen, whereas the London, 2009, mentioned above in the context of "fillers." For liquid excipients, or excipients that might be better dispersed if provided in solution, the substance may be sprayed into a ribbon blender with a spray bar as a powdered composition is blending. In this way, a dry blended powder is still obtained, even though small amounts of liquid ingredients are absorbed in homogeneously.

Suitable flavorants can include, for example, flavors, such as, natural flavors, artificial flavors, and combinations thereof. Non-limiting examples of flavor oils include spearmint oil, cinnamon oil, oil of wintergreen (methyl salicylate), peppermint oil, clove oil, bay oil, anise oil, *eucalyptus* oil, thyme oil, cedar leaf oil, oil of nutmeg, allspice, oil of sage, mace, oil of bitter almonds, and *cassia* oil. Suitable flavoring agents also include, for example, artificial, natural and synthetic fruit flavors such as vanilla, citrus oils (e.g., lemon, orange, lime, and grapefruit), and fruit essences (e.g., apple, pear, peach, grape, strawberry, raspberry, cherry, plum, pineapple, and apricot), and the like, and combinations thereof.

Other flavorants and fragrant aromatics that may be included individually or in combination include, but are not limited to, anethole, menthol, menthone, menthyl acetate, eucalyptol, borneol, borneol acetate, camphor, 1,8-cineole, cinnamaldehyde, benzaldehyde, citral, thujone, eugenol, limonene, geraniol, citronellol, citronellal, pinene, linalool, thymol, carvone, caryophyllene, linalyl acetate, methyl salicylate, and mixtures thereof. Also, substances that provide scent and flavor include, but are not limited to, 3,3,5-trimethylcyclohexanol, methoxycyclohexanol, benzyl alcohol, anise alcohol, cinnamyl alcohol, β-phenyl ethyl alcohol (2-phenylethanol), cis-3-hexenol, musk xylol, isoeugenol, methyl eugenol, α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, hydroxycitronellal, benzaldehyde, methyl nonyl acetaldehyde, dodecanol, α-hexylcinnamic aldehyde, undecenal, heliotropin, vanillin, ethyl vanillin, methyl amyl ketone, methyl β-naphthyl ketone, methyl nonyl ketone, musk ketone, diacetyl, acetyl propionyl, acetyl butyryl, acetophenone, p-methyl acetophenone, ionone, methyl ionone, amyl butyrolactone, diphenyl oxide, methyl phenyl glycidate, γ-nonyl lactone, coumarin, cineole, ethyl methyl phenyl glycidate, methyl formate, isopropyl formate, linalyl formate, ethyl acetate, octyl acetate, methyl acetate, benzyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myristate, methyl myristate, ethyl benzoate, benzyl benzoate, methylcarbinylphenyl acetate, isobutyl phenylacetate, methyl cinnamate, cinnamyl cinnamate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, β-phenylethyl acetate, trichloromethylphenyl carbinyl acetate, terpinyl acetate, vetiveryl acetate, and mixtures thereof.

Suitable sweeteners include nutritive carbohydrates such as sucrose, glucose, fructose, glucose, trehalose, galactose, mannitol, sorbitol, xylitol and artificial sweeteners such as saccharin, aspartame, acesulfame K, cyclamates, neotame, sucralose, *stevia*, and neohesperidin dihydrochalcone (NHDC).

Suitable buffers may comprise one or more acidifying agents or alkaline agents as necessary to neutralize various co-ingredients, form salts of various co-ingredients, and/or achieve a particular pH target for the composition, such as to adjust the local environment in the GI tract as a dosage form dissolves. For liquid appetite suppressant compositions, it may be desirable to adjust the pH of the liquid composition. Combinations of various acidifying agents and alkaline agents may be used to create buffering systems that stabilize the desired final pH of the composition. Buffers may be mixed buffers, meaning that the alkaline agent is not necessarily the conjugate base of the acidifying agent.

Exemplary acidifying agents for use in the present compositions include, but are not limited to, organic acids of any molecular weight and mineral acids (inorganic acids), and mixtures thereof. Organic acids may include mono-carboxylic acids, di-carboxylic acids, or tri-carboxylic acids, and may be saturated or may have any degree of unsaturation. For example, organic acids for use in various embodiments of the composition in accordance to the present disclosure may include, but are not limited to, formic acid, carbonic acid, acetic acid, lactic acid, oxalic acid, propionic acid, valeric acid, enanthic acid, pelargonic acid, butyric acid, lauric acid, docosahexaenoic acid, eicosapentaenoic acid, pyruvic acid, acetoacetic acid, benzoic acid, salicylic acid, aldaric acid, fumaric acid, glutaconic acid, traumatic acid, muconic acid, malonic acid, malic acid, succinic acid, glutaric acid, adipic acid, pimelic acid, suberic acid, azelaic acid, abietic acid, pimaric acid, sebacic acid, phthalic acid, isophthalic acid, terephthalic acid, maleic acid, citric acid, and combinations thereof.

Exemplary alkaline materials include any organic amines, $NH_3$, alkali metal or alkaline earth hydroxide, any conjugate bases of any organic acids (e.g. R—COO$^-$), and any of the salts of carbonic acid, phosphoric acid, nitric acid and sulfuric acid, and any mixtures thereof. For example, alkaline materials for use in various embodiments of the composition in accordance with the present disclosure may include, but are not limited to, NaOH, KOH, $NH_3$, sodium acetate, sodium succinate, disodium succinate, monosodium citrate, disodium citrate, trisodium citrate, $NaH_2PO_4$, $Na_2HPO_4$, $Na_3PO_4$, $KH_2PO_4$, $K_2HPO_4$, $K_3PO_4$, $NaHSO_4$, $Na_2SO_4$, $KHSO_4$, $K_2SO_4$, $NaHCO_3$, $Na_2CO_3$, $KHCO_3$, $K_2CO_3$, $NaH_3P_2O_7$, $Na_2H_2P_2O_7$, $Na_3HP_2O_7$, $Na_4P_2O_7$, $KH_3P_2O_7$, $K_2H_2P_2O_7$, $K_3HP_2O_7$, $K_4P_2O_7$, and mixtures thereof. Any of these chemical species may exist as various hydrates when purchased as raw materials for use in the present compositions.

Exemplary colorants include the pharmaceutically acceptable colors used for capsules and tablet dosage forms, such as the US FDA certified colors, dyes and lakes for use in pharmaceutical capsules, tablets and syrups. These acceptable colorants include the inorganic pigments such as titanium dioxide, yellow iron oxide, red iron oxide and black iron oxide, the organic pigments such as D&C Red 36, Red 30 and Red 34, the solvent soluble colors D&C Yellow 11, Yellow 7, Red 27, Red 21, Red 17, Green 6, and Violet 2, and the water soluble colors D&C Green 8, Yellow 10, Yellow 8, Orange 4, Red 22, Red 28, Red 33, Green 5, quinoline yellow, FD&C Yellow 5, Yellow 6, Red 4, Red 40, Red 3, Green 3, Blue 1, Blue 2, and ponceau 4R, carmoisine, amaranth, patent blue V and black PN, and a number of "organic lakes."

Suitable disintegrants include, but are not limited to, sodium starch glycolate, croscarmellose sodium, microcrystalline cellulose, and crospovidone. Some substances known to be disintegrants can act as CDRAs as well, since the swelling of an ingredient can not only break apart other structures but can occlude drug actives. For a review of disintegrants that find use in the present compositions, see P.

M. Desai, "Review of Disintegrants and the Disintegration Phenomena," *J. Pharm. Sci.*, 105, 2545-2555 (2016).

Suitable intestinal permeation enhancers include, but are not limited to surfactants that assist bio-absorption, including, for example, fatty acids and/or esters or salts thereof, bile acids and/or salts thereof. Bile acids/salts and fatty acids and their uses are further described in U.S. Pat. No. 6,287,860, which is incorporated herein in its entirety. In some embodiments, the present disclosure provides combinations of absorption enhancers, for example, fatty acids/salts in combination with bile acids/salts. An exemplary combination is the sodium salt of lauric acid, capric acid and ursodeoxycholic acid (UDCA) for promoting improved intestinal absorption of peptides and other materials. These excipients may be used in the present compositions to assist absorption of the AAI and/or the protein source, such as hydrolyzed animal or plant proteins. Further penetration enhancers include, but are not limited to, polyoxyethylene-9-lauryl ether, polyoxyethylene-20-cetyl ether. For a review of absorption enhancers that find use herein, see B. J. Aungst, "Intestinal Permeation Enhancers,"*J. Pharm. Sci.*, 89(4), 429 (2000).

Stabilizers and preservatives are generally more important for liquid compositions rather than dry powder compositions. Such substances for oral compositions include the parabens, sorbitol, sodium benzoate, benzoic acid, sorbic acid, potassium sorbate, propionic acid, and combinations thereof. Antioxidants include, but are not limited to, vitamin C, vitamin E, butylated hydroxyanisole (BHA), butylated hydroxytoluene (BHT), and propylgallate. In some instances, the antioxidant, such as a vitamin, can double as a nutritive substance in the appetite suppressant composition. For a review see, I. Himoudy, "Preservatives and their role in pharma and clinical research," *International Journal of Pharma Sciences and Scientific Research*, 2:4, 134-151 (2016).

The appetite suppressant compositions of the present disclosure may also include surfactants. The use of surfactants in drug products, formulations and in emulsions is well known in the art. Surfactants and their uses are further described in U.S. Pat. No. 6,287,860, which is incorporated herein in its entirety.

Exemplary Compositions, Dosage Forms, and Methods of Administration

Table 2 sets forth exemplary appetite suppressant compositions in accordance with the present disclosure. Each of these compositions are obtained by dry-blending each of the dry ingredients in a V-blender (e.g., MAXIBLEND® lab blender) or other suitable mixer configured for mixing dry ingredients. Liquid colorants may be sprayed into the blender with a spray nozzle. Each of the exemplary composition in Table 2 appear as loose powders and each were filled into two-piece hard shell capsules at the fill weights indicated.

TABLE 2

Exemplary Appetite Suppressant Compositions and Dosages:

| Ingredient (wt. %) | Composition | | | | | | | | |
|---|---|---|---|---|---|---|---|---|---|
| | 1 | 2 | 3 | 4 | 5 | 6 | 7 | 8 | 9 |
| AAI | 4.80[1] | 7.35[1] | 14.42[1] | 13.50[1] | 15.37[2] | 9.10[3] | 25.41[3] | 42.95[4] | 63.57[4] |
| CDRA | 44.62[5] | 45.50[5] | 44.62[5] | 40.34[5] | -0- | -0- | 47.42[5] | 57.01[6] | 36.40[6] |
| Nutritive[7] | 50.50 | 47.07 | 40.88 | 46.10 | 84.55 | 54.50 | 10.16 | -0- | -0- |
| Cofactor[8] | 0.08 | 0.08 | 0.08 | 0.06 | 0.08 | 0.07 | 0.07 | -0- | -0- |
| Excipients[9] | -0- | -0- | -0- | -0- | -0- | 36.33 | 16.94 | 0.04 | 0.03 |
| Total | 100% | 100% | 100% | 100% | 100% | 100% | 100% | 100% | 100% |
| Capsule Fill | 260 mg | 255 mg | 260 mg | 347mg | 260 mg | 275 mg | 295mg | 256 mg | 346 mg |

TABLE 2 notes: (1) preferably phentermine-HCl; (2) preferably phendimetrazine tartrate; (3) preferably diethylpropion-HCl with 1% tartaric acid; (4) preferably a 1:10 ratio of naltrexone-HCl to bupropion-HCl; (5) preferably hydroxypropyl methylcellulose; (6) preferably a 10:1 to about a 3:1 ratio of hydroxypropyl methylcellulose and microcrystalline cellulose; (7) preferably hydrolyzed collagen; (8) preferably chromium picolinate; and (9) preferably combinations of peppermint flavorant and/or colorants. The empty gelatin capsules used in these examples were size 1 (70 mg empty) and size 0 (90 mg empty).

Besides cellulosic CDRAs, which arguably are fillers in a sense, being non-digestive, the appetite suppressant compositions of Table 2 are absent inert fillers typically used in capsule and other oral dosage forms to provide bulk and weight. Thus, in various embodiments, appetite suppressant compositions according to the present disclosure comprise no inert filler.

In various embodiments, the AAI is selected from the group consisting of diethylpropion, amphetamine, benfluorex, bupropion, butanolide, caffeine, cathine, cetilistat, clobenzorex, D-fenfluramine, racemic-fenfluramine, ephedrine, etilamfetamine, exenatide, FG-7142 (diazepine inverse agonist), higenamine, liraglutide, lorcaserin, mazindol, mefenorex, metformin, methamphetamine, naltrexone, nicotine, orlistat, phenmetrazine, phendimetrazine, phentermine, phenylpropanolamine, pramlinatide, pseudoephedrine, pyroglutamyl-histidyl-glycine, rimonabant, semaglutide, sibutramine, topiramate, yohimbine, pro-drugs thereof, pharmaceutically acceptable salts thereof, and combinations thereof.

In various embodiments, the CDRA, when present for a controlled release composition, is selected from the group consisting of agar, agarose, albumin, alginate, casein, chitin, chondroitin, dextrin, fibroin, fucoidan, galactan, gellan, guar, scleroglucan, pullulan, xyloglucan, pectin, xanthan, psyllium, silica gel, fumed silica, magnesium aluminum silicate, clay, bentonite, hectorite, mesoporous silica, cellulose, cellulose acetate, hyaluronan, elastin-like polypeptides, β-cyclodextrin, collagen, gelatin, chitosan, carrageenan, polylactic acid, polyglycolic acid, poly(lactic-glycolic acid) (PLGA), poly(2-hydroxyethyl methacrylate), poly(2-hydroxypropyl methacrylate), poly(acrylic acid), carboxymethyl cellulose, carboxyethyl cellulose, hydroxyethyl cellulose, hydrophobically-modified hydroxyethyl cellulose, hydroxypropyl cellulose, hydroxypropyl methyl cellulose, methyl cellulose, ethyl cellulose, microcrystalline cellulose, nitrocellulose, polyvinyl alcohol, polyvinylpyrrolidone, polyvinylmethacrylate, carboxyvinyl polymers, polyvinylacetate, polyvinyl co-polymers, starch, modified starches, and combinations thereof.

In various embodiments, the nutritive, when present, is selected from the group consisting of a dried *Spirulina* algal species biomass powder, a dried *Chlorella* algal species biomass powder, a hydrolyzed powdered bovine or fish collagen, a bovine or porcine gelatin powder, egg albumin powder, calcium caseinate powder, powdered milk protein concentrate, whey protein isolate powder, yellow pea protein isolate, and combinations thereof.

In various embodiments, the cofactor, when present, is selected from the group consisting of calcium acetate, calcium ascorbate, calcium citrate, calcium gluconate, calcium nicotinate, calcium picolinate, chromium acetate, chromium ascorbate, chromium citrate, chromium gluconate, chromium nicotinate, chromium picolinate, copper acetate, copper ascorbate, copper citrate, copper gluconate, copper nicotinate, copper picolinate, magnesium acetate, magnesium ascorbate, magnesium citrate, magnesium gluconate, magnesium nicotinate, magnesium picolinate, manganese acetate, manganese ascorbate, manganese citrate, manganese gluconate, manganese nicotinate, manganese picolinate, potassium acetate, potassium ascorbate, potassium citrate, potassium gluconate, potassium nicotinate, potassium picolinate, selenium acetate, selenium ascorbate, selenium citrate, selenium gluconate, selenium nicotinate, selenium picolinate, zinc acetate, zinc ascorbate, zinc citrate, zinc gluconate, zinc nicotinate, zinc picolinate, and mixtures thereof.

In various embodiments, the excipients, when present, are selected from the group consisting of flavorants, colorants, and mixtures thereof.

With reference to TABLE 2, compositions 1-7 each benefit from the unusual combination of hydrolyzed bovine collagen and chromium picolinate in an extended release oral dosage form. This combination unexpectedly provides synergistic maintenance of a healthy gut barrier, along with increasing metabolism, stabilizing blood sugar levels, promoting weight loss and body fat, while increasing lean body mass. The combination further appears to improve skin elasticity, improve hair and nail appearance, improve muscle mass, improve heart health, relieve joint pain, and prevent bone loss. The hydrolyzed bovine collagen and chromium picolinate in an extended release oral dosage form appears to reduce hunger and cravings, and lower appetite, over extended periods of time, and may enhance insulin.

The appetite suppressant compositions of the present disclosure may be administered in a number of ways depending upon whether local or systemic treatment is desired. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Appetite suppressant compositions for topical administration may include transdermal patches, ointments, lotions, creams, gels, drops, suppositories, sprays, liquids and powders. Conventional pharmaceutically acceptable carriers, aqueous, powder or oily bases, thickeners and the like, may be necessary or desirable. In various embodiments, appetite suppressant compositions comprise loose powders that are filled into dissolvable capsules for oral administration and gastrointestinal absorption.

The appetite suppressant compositions of the present disclosure, which may conveniently be presented in unit dosage form such as a capsule, may be prepared according to conventional techniques well known in the pharmaceutical industry. Such techniques include the step of bringing into association the at least one AAI with the pharmaceutically acceptable carrier(s) or excipient(s), which in various embodiments comprises a nutritive base. In general, the appetite suppressant compositions are prepared by uniformly and intimately bringing into association the AAI(s) with finely divided solid carriers or both, and then, if necessary, shaping the product by addition of various excipients.

The appetite suppressant compositions of the present disclosure may be formulated into any of many possible dosage forms such as, but not limited to, tablets, capsules, gel capsules, liquids, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension or help to stabilize the suspension.

One of skill in the art will recognize that compositions are routinely designed according to their intended use, i.e., route of administration.

Appetite suppressant compositions for oral administration include powders or granules, microparticulates, nanoparticulates, capsules, gel capsules, sachets, tablets or minitablets. Oral formulations are those in which at least one AAI of the present disclosure is administered in conjunction with one or more CDRAs, surfactants, chelators, bio-absorption promotors such as intestinal permeation enhancers, or other active or nonactive excipients.

Dosage Regimens

In various embodiments of, methods of appetite suppression are described. In general, a method of suppressing appetite in an individual in need thereof comprises orally administering to the individual a therapeutically effective amount of an appetite suppressant composition comprising at least one AAI. In various embodiments, the individual in need thereof has been diagnosed as overweight and obese, as per ICD-10 code E66 and subgroups. This diagnosis is discussed in S. B. Gribsholt, et al., "Validity of ICD-10 diagnoses of overweight and obesity in Danish hospitals," *Clin. Epidemiol.*, 11, 845-854 (2019).

In various embodiments, a method of suppressing appetite in an individual in need thereof comprising orally administering to the individual a therapeutically effective amount of an appetite suppressant composition comprising: at least one AAI; at least one of a nutritive substance, a CDRA, and a cofactor; and optionally an excipient. In various embodiments, the AAI is selected from the group consisting of diethylpropion, amphetamine, benfluorex, bupropion, butanolide, caffeine, cathine, cetilistat, clobenzorex, D-fenfluramine, racemic-fenfluramine, ephedrine, etilamfetamine, exenatide, FG-7142 (diazepine inverse agonist), higenamine, liraglutide, lorcaserin, mazindol, mefenorex, metformin, methamphetamine, naltrexone, nicotine, orlistat, phenmetrazine, phendimetrazine, phentermine, phenylpropanolamine, pramlinatide, pseudoephedrine, pyroglutamyl-histidyl-glycine, rimonabant, semaglutide, sibutramine, topiramate, yohimbine, pro-drugs thereof, pharmaceutically acceptable salts thereof, and combinations thereof. In various embodiments, the AAI is selected from the group consisting of phentermine, diethylpropion, phendimetrazine, bupropion, naltrexone, prodrugs thereof, pharmaceutically acceptable salts thereof, and combinations thereof.

Appetite suppressant compositions of the present disclosure may be delivered orally, in granular form including sprayed dried particles, or complexed to form micro or nanoparticles, which may be administered as a loose powder that can be mixed into a beverage, or packed into capsules for swallowing. In various embodiments, the appetite suppressant composition comprise dry blended loose powders, with the dosage form comprising a capsule comprising the dry blended loose powder contained therein.

Capsule dosages are in large part based on the AAI(s) present in the powder composition within the capsule. Generally, the following dosage regimens apply for those individuals in need thereof that received ICD-10 diagnosis:

Phentermine—dosing up to 75 mg daily, with a time period of up to twice daily;

Diethylpropion—dosing up to 150 mg daily, with a time period of up to four times daily;

Phendimetrazine—dosing up to 210 mg daily, with a time period of up to three times daily; and Bupropion/Naltrexone—dosing up to 400 mg/40 mg daily, with a time period of up to twice daily.

For the preferred AAIs in the compositions and capsules outlined in Table 2, the following amounts and dosages are relevant:

Composition 1: each capsule contains 12.5 mg phentermine-HCl. Thus, a therapeutically effective amount of composition 1 comprises from 1 up to about 6 capsules per day;

Composition 2: each capsule contains 18.8 mg phentermine-HCl. Thus, a therapeutically effective amount of composition 2 comprises from 1 up to about 4 capsules per day;

Composition 3: each capsule contains 37.5 mg phentermine-HCl. Thus, a therapeutically effective amount of composition 3 comprises from 1 to about 2 capsules per day;

Composition 4: each capsule contains 46.9 mg phentermine-HCl. Thus, a therapeutically effective amount of composition 4 comprises from 1 to about 2 capsules per day;

Composition 5: each capsule contains 40 mg phendimetrazine tartrate. Thus, a therapeutically effective amount of composition 5 comprises from 1 up to about 5 capsules per day;

Composition 6: each capsule contains 25 mg diethylpropion-HCl. Thus, a therapeutically effective amount of composition 6 comprises from 1 up to about 6 capsules per day;

Composition 7: each capsule contains 75 mg diethylpropion-HCl. Thus, a therapeutically effective amount of composition 7 comprises from 1 up to about 2 capsules per day;

Composition 8: each capsule contains 10 mg naltrexone-HCl and 100 mg bupropion-HCl. Thus, a therapeutically effective amount of composition 8 comprises from 1 up to about 4 capsules per day; and Composition 9: each capsule contains 20 mg naltrexone-HCl and 200 mg bupropion-HCl. Thus, a therapeutically effective amount of composition 9 comprises from 1 up to about 2 capsules per day.

Appetite suppressant compositions and methods thereof are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a composition or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. An appetite suppressant composition consisting essentially of:
   from 12.0 wt. % to 18.0 wt. % phendimetrazine tartrate;
   from 80.0 wt. % to 90.0 wt. % bovine collagen; and
   from 0.05 wt. % to 0.10 wt. % chromium picolinate.

2. A pharmaceutical dosage form for oral administration comprising: a capsule; and the appetite suppressant composition of claim 1 enclosed therein.

3. A method of suppressing appetite in an individual, the method comprising orally administering to the individual in need thereof a therapeutically effective amount of the appetite suppressant composition of claim 1.

4. The method of claim 3, wherein the therapeutically effective amount comprises orally administering up to 210 mg per day of the phendimetrazine tartrate.

5. The method of claim 3, wherein the individual in need thereof is diagnosed overweight and obese.

6. An appetite suppressant dosage form consisting essentially of:
- 250 mg to 300 mg of the composition of claim 1 as a loose powder; and
- a dissolvable capsule encapsulating said composition.

7. An appetite suppressant composition consisting essentially of:
- from 6.0 wt. % to 12.0 wt. % diethylpropion-HCl, said diethylpropion-HCl including 1% tartaric acid;
- from 50.0 wt. % to 58.0 wt. % bovine collagen; and
- from 0.05 wt. % to 0.10 wt. % chromium picolinate.

8. A pharmaceutical dosage form for oral administration comprising: a capsule; and the appetite suppressant composition of claim 7 enclosed therein.

9. A method of suppressing appetite in an individual, the method comprising orally administering to the individual in need thereof a therapeutically effective amount of the appetite suppressant composition of claim 7.

10. The method of claim 9, wherein the therapeutically effective amount comprises orally administering up to 150 mg per day of the diethylpropion-HCl.

11. The method of claim 9, wherein the individual in need thereof is diagnosed overweight and obese.

12. An appetite suppressant dosage form consisting essentially of:
- 250 mg to 300 mg of the composition of claim 7 as a loose powder; and
- a dissolvable capsule encapsulating said composition.

* * * * *